Figure 1:
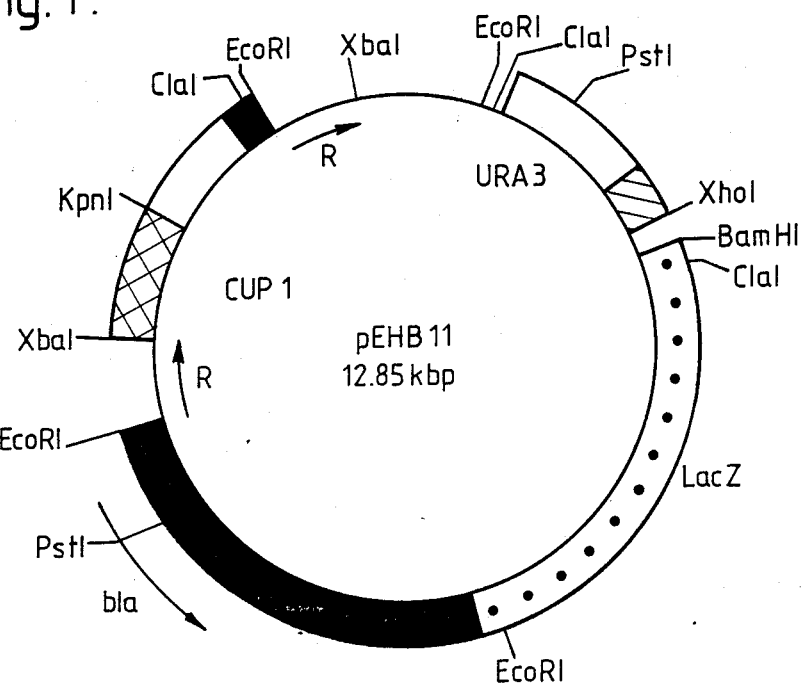
Figure 1:
Figure 1:
Figure 1:
Figure 1:
Figure 1:
Figure 1:
Figure 1:
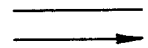

United States Patent [19]

Hinchliffe et al.

[11] Patent Number: 4,937,193
[45] Date of Patent: Jun. 26, 1990

[54] PROCESS FOR THE GENETIC MODIFICATION OF YEAST

[75] Inventors: Edward Hinchliffe, Burton Joyce; Christine J. Fleming, Leicestershire, both of England

[73] Assignee: Delta Biotechnology Limited, Burton-on-Trent, England

[21] Appl. No.: 66,931

[22] Filed: Jun. 26, 1987

[30] Foreign Application Priority Data

Jun. 27, 1986 [GB] United Kingdom ................ 8615701

[51] Int. Cl.$^5$ ...................... C12P 21/00; C12P 21/02; C12N 15/00
[52] U.S. Cl. ................................ 435/172.3; 435/320; 435/255; 435/257; 435/69.6; 935/28; 935/56; 935/69
[58] Field of Search ................... 435/68, 172.1, 172.3, 435/320, 317.1, 940; 935/28, 56, 69

[56] References Cited

U.S. PATENT DOCUMENTS 4,775,622 10/1988 Hitzeman et al. ...................... 435/68

OTHER PUBLICATIONS

Constructing of a Yeast Plasmid Cloning Vector with High Stability in Saccharomyces Strains Deficient in 2-μm.—GB 2 175 590.
Cloning with 2-μm DNA Vectors and the Expression of Foreign Genes in Saccharomyces Bachmair & Ruis (1984) Monatshefte fur Chemie 115, 1229-11235.
Jayaram, M., Association of Reciprocal Exchange with Gene Conversion Between the Repeated Segments of 2-μm Circle; J. Mol. Biol. 191, p. 341 (1986).
Henderson, R. C. A.; The Transformation of Brewing Yeasts with a Plasmid Containing the Gene for Copper Resistance; Current Genetics 9, pp. 133-138 (1985).
Jayaram, M.; Mating Type-Like Conversion Promoted by 2 micron specific recombinase; Molec. Cell. Biol. 6 (11), pp. 3831-3837 (1986).
Struhl, K.; Direct Selection for Gene Replacement Events in Yeast; Gene 26, pp. 231-242 (1983).

Primary Examiner—Robin Teskin
Attorney, Agent, or Firm—Cushman, Darby & Cushman

[57] ABSTRACT

Yeast is genetically modified by transformation with an integration vector comprising two copies of a homologous 2 μm plasmid DNA sequence in direct orientation relative to one another and encompassing the said DNA sequence, and then isolating, from the transformed yeast obtained, cells containing the endogenous 2 μm plasmid modified by incorporation of the said DNA sequence but not containing the said vector. The resulting yeast can be maintained under non-selective growth conditions.

14 Claims, 2 Drawing Sheets

CUP 1 gene of yeast.

Chromosomal DNA of yeast.

GAL 10/CYC1 hybrid promoter.

LacZ gene of E.coli encoding β-galactosidase.

E.coli plasmid DNA

2μm plasmid DNA sequences.

R 703 base-pair DNA sequence from 2μm arrows indicate orientation.

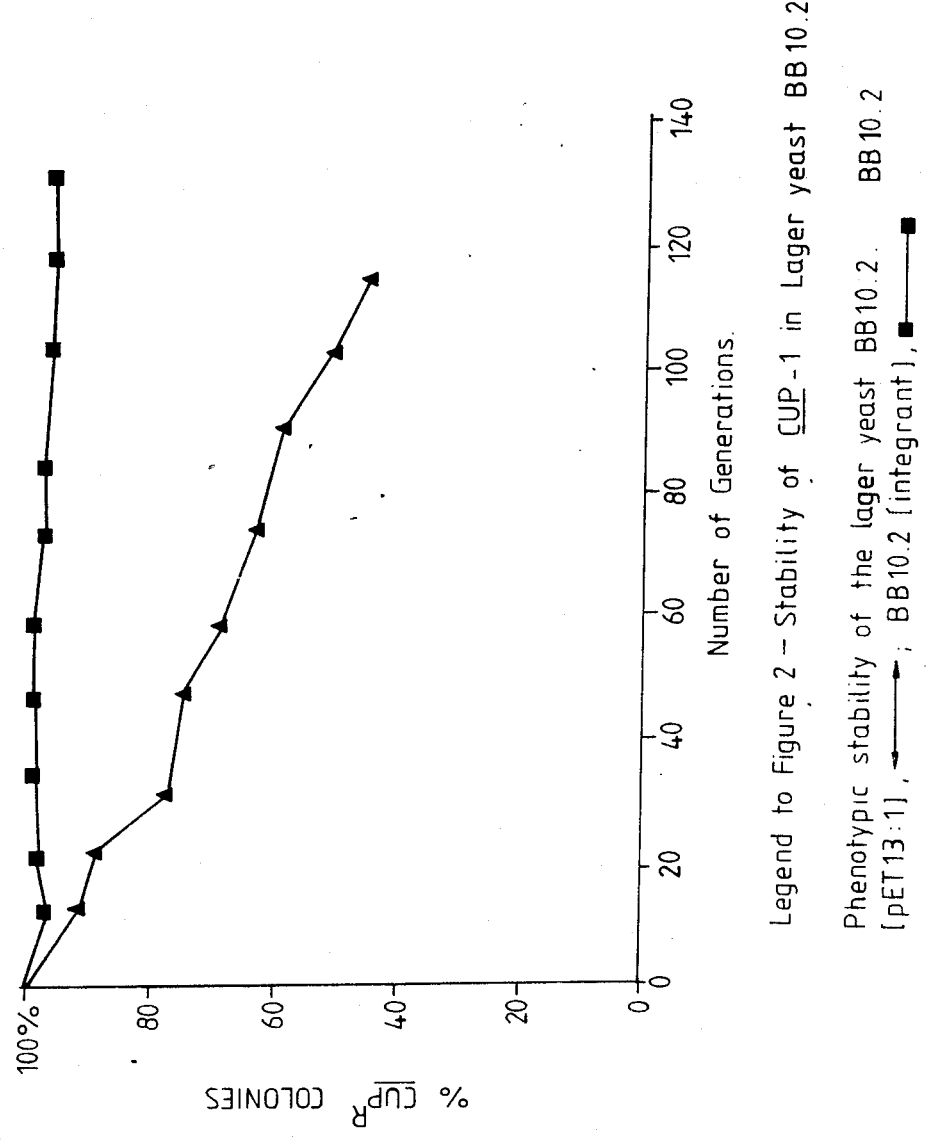

PROCESS FOR THE GENETIC MODIFICATION OF YEAST

This invention relates to genetic engineering in brewing yeast.

The introduction of recombinant DNA into laboratory strains of yeast by the process of transformation is commonplace, and has developed considerably in sophistication since the phenomenon was first reported in the late nineteen seventies (Hinnen et.al, 1978; Beggs, 1978). Vectors commonly in use for yeast transformation can be divided into two types:

(i) replicating vectors, that is those which are capable of mediating their own maintenance independent of the chromosomal DNA of yeast by virtue of the presence of a functional origin of DNA replication; and (ii) integrating vectors which rely upon recombination with the chromosomal DNA to facilitate replication and thus the continued maintenance of the recombinant DNA in the host cell. Replicating vectors can be further sub-divided into:

(a) 2 $\mu$m-based plasmid vectors in which the origin of DNA replication is derived from the endogenous 2 $\mu$m plasmid of yeast;

(b) autonomously replicating vectors (ARS) in which the "apparent" origin of replication is derived from the chromosomal DNA of yeast and (c) centromeric plasmids (CEN) which carry in addition to one of the above origins of DNA replication a sequence of yeast chromosomal DNA known to harbour a centromere.

In order to transform yeast efficiently with any of the aforementioned vectors it is necessary to impose on the dividing yeast cells a selection to identify those transformants which carry the recombinant DNA. This is achieved in laboratory yeast by incorporating within the vector DNA a prototrophic gene, which complements an auxotrophic mutation in a chosen recipient strain. Such plasmid vectors are therefore only of value in effecting the transformation of laboratory mutant auxotrophic yeast. In order to transform brewing yeast, which are polyploid and do not display auxotrophic requirements, it is necessary to utilize a selection system based upon a dominant selectable gene. In this respect replicating 2$\mu$m-based plasmid vectors have been described carrying genes which mediate resistance to:

(i) antibiotics, for example G418 (Jiminez et.al., 1980; Webster et.al., 1983), hygromycin B (Gritz et.al., 1983), chloramphenicol (Cohen et.al., 1980) and (ii) otherwise toxic materials, for example, the herbicide sulfometuron methyl (resistance mediated via a mutant yeast $\beta$-acetolactate synthase gene, ILV-2) (Falco et.al., 1985) and copper (resistance mediated via the CUP-1 gene of yeast) (Henderson et.al., 1985).

In all cases in which yeasts have been transformed with replicating plasmid vectors, the stability of the transformed phenotype is low under non-selective conditions of cell growth. Thus 2 $\mu$m-based vectors are lost from recipient laboratory yeast strains at a frequency of approximately 1–5% per cell doubling in the absence of selection (Beggs, 1978; Broach et.al., 1979; Gerbaud et.al., 1979; Struhl et.al., 1979).

The relative stability of such plasmids in yeast is dependent upon the yeast host. In this respect, it has been shown that 2 $\mu$m-based plasmids conferring resistance to copper in brewing yeast are lost at a frequency of approximately 0.18% per cell doubling (Hinchliffe & Daubney, 1986). Similarly, just as the recipient yeast can influence plasmid stability, the nature of the plasmid itself has an important role to play. ARS plasmids, for example, are lost at a frequency greater than 10% per cell doubling (Kikuchi, 1983). In order to ensure the stable maintenance of the transformed phenotype following continuous cell proliferation, it is necessary to maintain selection for the plasmid. In the case of laboratory yeast transformants this imposes limitations on the nature of the medium available for cell growth, since it is usually necessary to select on minimal medium lacking the nutrient which is required by the recipient yeast. In the case of brewing yeast transformants, however, it is both impracticable and undesirable to supplement the normal growth medium, hopped brewers wort, with either antibiotics or 'toxic' materials, such as copper ions, since these materials are expensive and are likely to have a deleterious effect upon the quality of the beer which is the primary product of the fermentation.

One approach to ensure the maintenance of recombinant genes in yeast, under non-selective growth conditions, is to use integrating yeast vectors, which, when introduced into the recipient, enter the host chromosome by genetic recombination between homologous sequences on the vector and the chromosomal DNA. However, such vectors have an extremely low efficiency of transformation, and give rise to only about 1–10 transformants per $\mu$g of DNA (Hinnen et.al., 1978; Hicks et.al., 1979). This frequency can be improved by cleaving the DNA to be transformed with a restriction endonuclease which cuts in the region of DNA homology, as this creates a highly recombinogenic molecule (Hicks et.al., 1979). This phenomenon implies that the major factor limiting the efficiency of transformation with integrating vectors is not DNA uptake but rather recombination. This need not restrict the application of an integrating vector system to brewing yeast providing that the target DNA sequence for recombination is in a region which does not affect the metabolism of the host cell. Thus an integrating yeast vector has recently been described for application in brewing yeast based upon the principles described above (Yeast Vector, European Pat. Publication No. 163,491, Biotechnica International Inc.). While this system confers gene stability in brewing yeast, it does not facilitate high copy number maintenance of recombinant DNA and is potentially more difficult to implement because of the intrinsically low transformation efficiency of brewing yeast.

The present invention provides a process for the transformation of yeast, in particular brewing yeast, with a 2 $\mu$m-based recombinant plasmid. The transformation of brewing yeast may be facilitated by the presence of the CUP-1 gene of yeast on the plasmid, enabling selection for copper resistant transformants, but any dominant selectable marker, including antibiotic resistance, can be used, and indeed the use of a separate marker gene, as distinct from a gene coding for the peptide product of interest, may be dispensed with altogether. Stable maintenance of a recombinant 'gene of interest' is achieved by directing the integration of the 'gene' by genetic recombination to a site within the endogenous 2 $\mu$m plasmid of brewing yeast. This plasmid is present in all proprietary strains of yeast thus far investigated (Hinchliffe & Daubney, 1986). The ubiquitous nature of the endogenous 2 $\mu$m plasmid implies that this plasmid is stably maintained in brewing yeast through many generations of apparently non-selective growth. Thus ideally the integration of the 'gene(s) of interest' should be directed to a site within the 2 μm plasmid which does not adversely influence the inherent stability of the endogenous 2 μm plasmid.

The 2 μm plasmid of yeast is a circular DNA molecule of 6318 base-pairs for which the entire nucleotide sequence has been determined (Hartley & Donelson, 1980). It is present in approximately 50-100 copies per cell in most strains of *Saccharomyces cerevisiae* (Clarke-Walker & Miklos, 1974), including brewing yeast (Aigle et.al., 1984; Hinchliffe & Daubney, 1986). The plasmid is inherited in a non-Mendelian fashion (Livingston, 1977), and for this reason it has been regarded as cytoplasmic in cell location. However, a significant body of data exists which indicates that the plasmid is located in the nucleus (Nelson & Fangman, 1979; Livingston & Hahne, 1979; Seligy et.al., 1980; Taketo et.al., 1980; Sigurdson et.al., 1981). An important feature of the plasmid is the presence of two inverted repetitions (599 base-pairs in length) which separate the molecule into two unique regions. Intramolecular recombination between the inverted repeats results in the inversion of one unique region relative to the other and the production in vivo of a mixed population of two structural forms of the plasmid, designated A and B (Beggs, 1978). Recombination between the two inverted repeats is mediated by the product of a gene entitled FLP which is present on the plasmid itself. The FLP gene encodes a protein which is capable of mediating high frequency recombination between the inverted repeat region.

It has surprisingly been found that a "gene of interest" can be incorporated in a 2 μm in a way which does not adversely influence the inherent stability of the endogenous 2 μm plasmid.

According to the present invention, a process for the genetic modification of yeast by the incorporation into the endogenous 2 μm plasmid of yeast a DNA sequence coding for a protein or peptide of interest comprises first transforming yeast with an integration vector comprising two copies of homologous 2 μm plasmid DNA sequences positioned in direct orientation relative to one another and encompassing the said DNA sequence and then isolating, from the transformed yeast obtained, cells containing the endogenous 2 μm plasmid modified by incorporation of the said DNA sequence but not containing the vector. The DNA sequence of interest may be incorporated in the integration vector via an appropriate restriction site, for example a Bam HI site or a Kpn I site, at which a DNA sequence of interest can be inserted. The vector usually also comprises an extraneous DNA sequence, i.e. a sequence not necessary or over desirable for the propagation of the plasmid in yeast, but desirable for the reasons, e.g. propagation in bacteria or other non-yeast host microorganism. This extraneous DNA sequence is separated from the DNA sequence coding for the protein or peptide of interest by the homologous sequence in direct orientation. Preferably the extraneous DNA sequence is a DNA sequence heterologous to yeast which assists propagation of the vector in bacteria.

The invention also provides a 2 μm plasmid integration vector which comprises two copies of a 2 μm homologous DNA sequence in direct orientation, a DNA sequence, usually heterologous to yeast, which assists propagation of the plasmid outside yeast, and a DNA sequence coding for a heterologous protein or peptide of interest separated from the said DNA sequence assisting propagation of the plasmid by the said homologous sequences in direct orientation.

In the process of the invention, integration occurs via a recombination event and results in the integration of the recombinant gene (i.e. the DNA sequence of interest) to the exclusion of the remainder of the vector DNA not encompassed between the homologous DNA repeat sequences of the vector. This process ensures that only the 'gene(s) of interest' is stably maintained for successive generations in yeast, e.g. brewing yeast, under non-selective conditions of growth, and thereby circumvents any deleterious effects that additional DNA sequences may have upon either the technological behaviour of the yeast or the flavour and quality characteristics of the products, e.g. beer, produced by the yeast.

Although the present invention does not depend on the truth of this theory it is believed that the vector, upon introduction into yeast, undergoes an intramolecular recombination between the homologous DNA repeat sequences to produce two plasmid fragments, each containing one DNA sequence with homology to the endogenous 2 μm plasmid. One of these fragments carries a 2 μm origin of replication which was carried by the original vector and the other carries the other DNA sequence initially contained between the repeat sequences of the vector. Recombination of the latter plasmid fragment with an endogenous 2 μm plasmid of yeast at the region of homology produces a stable integrant which comprises the endogenous 2 μm plasmid of yeast and, inserted into the region of homology, the DNA sequence of interest originally contained between the two directly oriented repeats of homologous DNA of the vector.

In practice the 'gene(s) of interest' can be any recombinant gene, either homologous or, more usually, heterologous to yeast. The process may be used, for example, to integrate the Human Serum Albumin gene stably in brewing yeast so that it is expressed from either a constitutive yeast promoter, for example the phosphoglycerate kinase promoter (PGK), or a regulated yeast promoter, for example the GAL10/CYC1 hybrid promoter as described in European Pat. Application No. 86303039.1, published under No. 201239, "Fermentation with an Inducible Gene Expression System" (Delta Biotechnology Ltd.) or the GAL10/PGK promoter (PAL) described in British Pat. Application No. 8620926 filed Aug. 29th, 1986 "Yeast Promoter" (Delta Biotechnology Ltd.).

Other genes which can be stably integrated by this system include the DEX-1 gene of *Saccharomyces diastaticus* which specifies the production of an extracellular glucoamylase enzyme in brewing yeast and the β-glucanase gene of *Bacillus subtilis* which specifies the production of an endo-1,3-1,4-β-glucanase in brewing yeast (Hinchliffe & Box, 1985). Additional genes can be first genetically modified to control the level of gene expression or to ensure that the protein whose synthesis is mediated by the gene is secreted by the brewing yeast.

The gene integration process of the invention ensures stable maintenance of the 'gene(s) of interest' at a high copy number, under conditions of non-selective growth. This is particularly advantageous when implementing the process described in European Pat. Application No. 86303039.1 (Fermentation with an Inducible Gene Expression System), since under these circumstances the expression of the 'gene(s) of interest' is regulated so that it is not expressed during the course of the primary beer fermentation, but rather induced in a post-fermentation process. By ensuring high copy numbers of the 'gene(s) of interest' it is possible to achieve high level induction during the post-fermentation process, thereby enhancing the amount of heterologous protein produced.

The stable integration of the *Saccharomyces diastaticus* DEX-1 gene facilitates the production of beer with an enhanced attenuation limit, since the extracellular glucoamylase partially hydrolyses starch (dextrins) present in wort. Thus it is possible using this system to produce beer in which a portion of the non-fermentable starch is converted to fermentable sugar and thus to alcohol, without recourse to the addition of expensive commercial exogeneous enzymes.

EXAMPLE 1

Integration of the CUP-1 gene of yeast in the endogenous 2 μm plasmid of brewing yeast Plasmid pEHB11 (described in European Pat. Application No. 86303039.1, publication No. 201239, Fermentation with an Inducible Gene Expression System; Delta Biotechnology Ltd.) was transformed into the brewing yeast strains NCYC 240 (ale yeast—National Collection of Yeast Cultures, Colney Lane, Norwich, United Kingdom) and BB10.2 (lager yeast—a proprietary strain of Bass yeast) by selection for copper resistant transformants as described by Hinchliffe & Daubney (1986) NCYC 240 (pEHB11) has been deposited at the National Collection of Yeast Cultures, Colney Lane, Norwich, NR4 7AU, United Kingdom on Dec. 12th, 1984 under No. NCYC 1547.

Transformants were verified as being copper resistant (>1 mM $CuSO_4.7H_2O$), β-galactosidase positive (blue/green colour on M63, 2% w/v galactose and X-gal, European Pat. Application No. 86303039.1) and β-lactamase positive (Chevallier & Aigle, 1979). Transformants were grown in NEP, supplemented with 2% w/v glucose and 0.2mM $CuSO_4.7H_2O$ to late stationary phase prior to sub-culturing in non-selective medium (NEP, 2% w/v glucose lacking $CuSO_4.7H_2O$). Following approximately 15-20 cell doublings yeast were harvested and plated for single colonies on NEP, 2% w/v glucose agar medium. Single colonies were then checked for the phenotypic presence of the plasmid pEHB11 by replica plating to the same medium supplemented with 0.2 mM $CuSO_4.7H_2O$ and 1mM $CuSO_4.7H_2O$, as well as M63 medium supplemented with 2.0% w/v galactose and X-gal.

The results indicated that plasmid pEHB11 was unstable in each of the brewing yeasts since a high proportion of colonies were obtained which were both sensitive to copper and unable to produce a blue/green colouration on X-gal (β-galactosidase negative). This instability is as one would expect for a 2 μm-based plasmid in brewing yeast when grown non-selectively. However, in addition to the copper sensitive β-galactosidase negative colonies (pEHB11 minus) and the copper resistant β-galactosidase positive colonies (pEHB11 plus) a small proportion of colonies were obtained which retained resistance to 0.2mM $CuSO_4.7H_2O$ but did not produce β-galactosidase. This latter type of colony was isolated and further evaluated; genetic analysis revealed that they were incapable of producing any β-galactosidase or β-lactamase.

Copper resistant β-galactosidase negative cells were subjected to a full molecular biological analysis; total yeast DNA was isolated by the method of Cryer et.al., (1975), and digested with the restriction endonucleases Eco RI and Cla I. Digested and undigested DNA fragments were separated by agarose gel electrophoresis and transferred to nitrocellulose filters by the method of Southern (Maniatis et.al., 1982). Filters were then prehybridized in prehybridization buffer (5 mg salmon sperm DNA, 10 mg bovine serum albumin, 10 mg Ficoll, 10 mg polyvinyl pyrrolidone, 0.1 g glycine, in 10 ml of 50% v/v formamide: 100 mM phosphate pH 6.5 in 5×SSC (0.15M NaCl, 0.015M tri-sodium citrate, pH 7.0) for 1-2 hours at 42° C. prior to DNA:DNA hybridization with nick translated $P^{32}$ labelled DNA probes (Rigby et.al., 1977). Regions of DNA homology were identified by autoradiography. Hybridization to the 1.25 kilo-base-pairs Sau 3A fragment of pET13:1, carrying the CUP-1 gene (Henderson et.al., 1985), showed that the copper resistant β-galactosidase negative clones had a different hybridization pattern to that observed for brewing yeast transformants harbouring plasmid pEHB11. The hybridization pattern obtained was indicative of the integration of the CUP-1 sequence of pEHB11 into the endogenous 2 μm plasmid of the brewing yeast strain. Furthermore, hybridization to undigested DNA confirmed that the copper resistant β-galactosidase negative clones possessed a small plasmid of approximately 9.13 kilo-base-pairs carrying the CUP-1 gene, a composite between 2 μm (6.3 kilo-base-pairs) and the CUP-1 sequence contained within the direct repeats of homologous 2 μm DNA present on pEHB11, whereas plasmid pEHB11 has a size of approximately 12.85 kilo-base-pairs.

Further hybridizations of total genomic DNA with $^{32}P$ labelled plasmid pMC1403 DNA (Casadaban et.al., 1980) carrying the lac Z gene of *E. coli* and additional *E. coli* plasmid DNA sequences, indicated that the copper resistant β-galactosidase negative clones were devoid of substantially all of the bacterial DNA sequences carried by pEHB11.

The site of integration of the CUP-1 gene within the endogenous 2 μm plasmid of brewing yeast was shown to be within the region of DNA homology carried by the directly oriented DNA repeat sequences of pEHB11. This was determined by probing total DNA restriction digests with a $^{32}P$ labelled 2138 base-pair Eco RI - Hind III fragment derived from the plasmid pJDB110 (Beggs, 1981). This 2138 base-pair fragment harbours the origin of DNA replication of 2 βm B-form together with a single copy of the 'inverted' repeat DNA sequence. Thus integration of CUP-1 within a region of DNA immediately adjacent to one of the inverted repeats results in a perturbation of the normal restriction pattern observed following hybridization to Southern transfers. Standard restriction mapping coupled with Southern transfer and hybridization enabled the site of insertion to be localized within a 703 base-pair region of DNA bounded by an Eco RI site at coordinate O and an Xba I site at coordinate 703 of 2 μm B form (Broach 1981).

Stable High Copy Number Maintenance of the Integrated CUP-1 Gene

The inheritable stability of the copper resistant phenotype in the copper resistant β-galactosidase negative clones of brewing yeast, hereinafter referred to as 'integrants', was analysed after growth under non-selective conditions.

Integrants were isolated and cultured in 10ml NEP containing 2% w/v glucose and 0.2mM $CuSO_4.7H_2O$ to stationary phase. Yeast cells were then harvested by centrifugation and subcultured in fresh medium lacking copper sulphate. Yeast were grown to mid-exponential growth phase and then sub-cultured into fresh growth medium. The presence of the CUP-1 gene was monitored phenotypically by plating cells on NEP, 2% w/v glucose agar medium, followed by replica plating to the same medium supplemented with 0.5mM $CuSO_4.7H_2O$. This process of continuous growth under non-selective conditions was maintained for approximately 100-130 generations. The results presented in FIG. 2 demonstrate that the copper resistant phenotype was stable over this period. When the same experiment was performed using brewing yeast transformed with the $2\mu m$ recombinant plasmid pET13:1, a significant degree of inheritable instability was observed (FIG. 2). Further molecular characterization of the integrants by DNA hybridization with appropriately labelled DNA probes (as described previously) indicated that the CUP-1 gene was retained within the endogenous $2\mu m$ plasmid following continued growth under non-selective conditions.

Brewing yeast normally contains a single chromosomal copy of the CUP-1 gene located on a 5.2 kilobase-pair Eco RI fragment. Thus it is possible to determine the number of extrachromosomal copies of the CUP-1 gene present in the 'integrant' brewing yeast by probing Eco RI digested total yeast DNA with a $^{32}P$ labelled CUP-1 probe (e.g. 1.25 kilo-base-pair Sau 3A fragment from pET13:1, Henderson et.al., 1985). Such a hybridization results in two bands of DNA homology corresponding to the 5.2 kilo-base-pair chromosomal CUP-1 fragment and a 3.0 kilo-base-pair fragment derived from the CUP-1 gene integrated into the endogenous $2\mu m$ plasmid.

A comparison of the intensity of the two DNA bands by densitometric scanning of the exposed autoradiogram enables one to estimate the approximate copy number of the extrachromosomal CUP-1 gene relative to the number of chromosomal/genomic equivalents. In this way, it was estimated that the integrants possess approximately 87 copies of the extrachromosomal CUP-1 gene per CUP-1 genome equivalent.

An alternative method for measuring the copy number of the extrachromosomal CUP-1 gene, by comparing the relative intensity of homology of the CUP-1 gene to the re-iterated 5S ribosomal DNA of yeast (Petes, et al., 1985) gave a copy number estimate of 55 per haploid genome equivalent for an integrant; whereas BB10.2 harbouring pET13:1 had an extrachromosomal copy number of 42 per haploid genome equivalent.

The Use of pEHB11 as a General 2 μm Integration Vector

Plasmid pEHB11 carries a unique KpnI restriction endonuclease site which is located within the directly oriented 703 base-pair homologous repeat, adjacent to the 3' terminus of the CUP-1 gene (FIG.1). This unique site can conveniently be used for the insertion of additional DNA sequences, for example a 'gene of interest', thereby enabling integration into the endogenous 2 μm plasmid of brewing yeast following successful transformation. By utilizing plasmid pEHB11 and its unique KpnI cloning site it is possible to integrate selectively a Human Serum Albumin (HSA) gene expressed from a regulated GAL10/CYC1 promoter-terminator expression cassette, thereby affording the high copy number stable maintenance of a regulated HSA expression unit. This facilitates a high level of gene expression when brewing yeast harbouring this integrated gene is induced for HSA production following postfermentation processing in accordance with the procedure outlined previously (European Pat. Application No. 86303039.1).

REFERENCES

Aigle et al., (1984), Journal of the American Society of Brewing Chemists, 42, 1.
Beggs, (1978), Nature, 275, 104.
Beggs (1981), In: "Molecular Genetics in Yeast" Alfred Benzon Symposium No:16, Munksgaard, Copenhagen.
Broach (1981), In: "The Molecular Biology of the Yeast Saccharomyces: Life Cycle and Inheritance", Eds. Strathern et al, Cold Spring Harbor, N.Y., pp 445.
Broach & Hicks, (1980), Cell, 21, 501.
Casadaban et al, (1980), Journal of Bacteriology, 143, 971.
Chevallier & Aigle, (1979), FEBS Letters, 108, 179.
Clark-Walker & Miklos, (1974), European Journal of Biochemistry, 41, 359.
Cohen et al, (1980), Proceeding of the National Academy of Sciences, U.S.A., 77, 1078.
Cryer et al, (1975), In: "Methods in Cell Biology", 12, Academic Press, pp.39-44.
Falco et al, (1985), Nucleic Acids Research, 13, 4011.
Gerbaud et al, (1979), Gene, 5, 233.
Gritz et al, (1983), Gene, 25, 178.
Hartley & Donalson, (1980), Nature, 286, 860.
Henderson et al, (1985), Current Genetics, 9, 133.
Hicks et al, (1979), Cold Spring Harbour Symposium Quantitative Biology, 43, 1305.
Hinchliffe & Box (1985). Proceeding of the European Brewery Convention Congress, 20th, Helsinki, 267.
Hinchliffe & Daubney (1986), Journal of the American Society of Brewing Chemists, 44, 98.
Hinnen et al, (1978), Proceedings of the National Academy of Sciences, U.S.A., 75, 1929.
Jiminez et al, (1980), Nature, 287, 869.
Kikuchi, (1983), Cell, 35, 487.
Livingston, (1977), Genetics, 86, 73.
Livingston & Hahne, (1979), Proceedings of the National Academy of Sciences, U.S.A., 76, 3727.
Maniatis et al. (1982), In: "Molecular Cloning a Laboratory Manual", Cold Spring Harbour.
Nelson & Fangman, (1979), Proceedings of the National Academy of Sciences, U.S.A., 76, 6515.
Petes et al. (1978), Journal of Bacteriology, 134, 295.
Rigby et al, (1977), Journal of Molecular Biology, 113, 237.
Seligy et al, (1980), Nucleic Acids Research, 8, 3371.
Sigurdson et al, (1981), Molecular and General Genetics, 183, 59.
Struhl et al, (1979), Proceedings of the National Academy of Sciences, U.S.A., 76, 1035.
Taketo et al, (1980), Proceedings of the National Academy of Sciences, U.S.A., 77, 3144.
Webster et al, (1983), Gene, 26, 243.

We claim:
1. A process for the genetic modification of yeast, the yeast comprising endogenous 2 μm plasmid, by incorporation into the endogenous 2 μm plasmid of a DNA sequence coding for a protein or peptide of interest which comprises first transforming yeast with an integration vector comprising two copies of a homologous 2 μm plasmid DNA sequence in direct orientation rela- tive to one another and encompassing the said DNA sequence, each of the said two homologous 2 μm plasmid sequences comprising a DNA fragment corresponding to a 703 base pair portion of the endogenous 2 μm plasmid bounded by XbaI and ECoRI restriction sites contained in pEHB11 depicted in FIG. 1, or a fragment thereof which is capable of enabling the DNA sequence coding for the peptide or protein of interest to be integrated into the endogenous 2 μm plasmid of said yeast and then isolating, from the transformed yeast obtained, cells containing the endogenous 2 μm plasmid modified by incorporation of the said DNA sequence but not containing the said vector.

2. Process according to claim 1 in which the integration vector also comprises an extraneous DNA sequence separated from the DNA sequence coding for the protein or peptide of interest by the said homologous sequences in direct orientation.

3. Process according to claim 2 in which the said extraneous DNA sequence is a DNA sequence heterologous to yeast which assists propagation of the vector in bacteria.

4. Process according to claim 1 in which the said vector also includes a selectable marker DNA sequence which is not separated from the DNA sequence which codes for the protein or peptide of interest by the homologous sequences in direct orientation.

5. Process according to claim 4 in which the selectable marker DNA sequence is a gene coding for resistance to copper.

6. Process according to claim 1 in which the said vector includes an origin of replication endogenous to the 2 μm plasmid of yeast.

7. Process according to claim 1 in which the DNA sequence coding for a protein or peptide of interest codes for human serum albumin.

8. Process according to claim 1 in which the yeast is brewing yeast.

9. A 2 μm plasmid vector for use in the process of claim 8 comprising two copies of a homologous 2 μm plasmid DNA sequence in direct orientation, each of said two homologous 2 μm plasmid sequences comprising a DNA fragment corresponding to a 703 base pair portion of the endogenous 2 μm plasmid bounded by XbaI and EcoRI restriction sites contained in pEHB11 depicted in FIG. 1, or a fragment thereof which is capable of enabling the DNA sequence coding for the peptide or protein of interest to be integrated into the endogenous 2 μm plasmid of said yeast, a DNA sequence that assists propagation of the plasmid outside yeast, and a DNA sequence coding for a heterologous protein or peptide of interest separated from said DNA sequence that assists propagation of the plasmid by said homologous sequences in direct orientation.

10. A 2 μm plasmid vector according to claim 9 in which also includes a selectable marker DNA sequence which is not separated from the DNA sequence which codes for the protein or peptide of interest by the homologous sequences in direct orientation.

11. A 2 μm plasmid vector according to claim 10 in which the selectable marker DNA sequence is a gene coding for resistance to copper.

12. A 2 μm plasmid vector according to claim 9 which includes an origin of replication endogenous to the 2 μm plasmid of yeast.

13. A 2 μm plasmid vector according to of claim 1 in which the heterologous protein or peptide of interest is human serum albumin.

14. A 2 μm plasmid vector according to claim 9 in which each of the homologous 2 μm plasmid sequences in direct orientation comprises said 703 base pair region of DNA.

* * * * *